(12) United States Patent
Moskowitz

(10) Patent No.: US 6,998,404 B2
(45) Date of Patent: Feb. 14, 2006

(54) TREATMENT OR PREVENTION OF ACUTE RENAL FAILURE

(75) Inventor: David W. Moskowitz, St. Louis, MO (US)

(73) Assignee: GenoMed, LLC, St. Louis, MO (US)

( * ) Notice: Subject to any disclaimer, the term of this patent is extended or adjusted under 35 U.S.C. 154(b) by 323 days.

(21) Appl. No.: 10/215,962

(22) Filed: Aug. 8, 2002

(65) Prior Publication Data

US 2003/0032650 A1 Feb. 13, 2003

Related U.S. Application Data

(60) Provisional application No. 60/310,686, filed on Aug. 8, 2001, and provisional application No. 60/352,075, filed on Jan. 28, 2002.

(51) Int. Cl.
*A61K 31/52* (2006.01)

(52) U.S. Cl. ..................................................... 514/263
(58) Field of Classification Search .................. 514/263
See application file for complete search history.

(56) References Cited

U.S. PATENT DOCUMENTS 5,786,360 A * 7/1998 Neely .......................... 514/263
6,313,131 B1 11/2001 Lawyer

OTHER PUBLICATIONS

Merck Manual, 15th edition, 1987, pp. 630–631.*
Neely, Am. J. Physiology, Jun. 1995, 268(6 pt 1) L1036–46, abstract.*
Bidani & Churchill, "Aminophylline ameliorates glycerol–induced acute renal failure in rats," *Can. J. Physiol. Pharmacol.* 61:567–571 (1983).
Bidani, et al., "Theophylline–induced protection in myoglobinuric acute renal failure: further characterization," *Can. J. Physiol. Pharmacol.* 65: 42–45 (1987).
Heidemann, et al., "Effect of aminophylline on cisplatin nephrotoxicity in the rat," *Br. J. Pharmacol.* 97:313–318 (1989).
Shohat, et al., "Lack of suppressor T cells in renal transplant recipients and activation by aminophylline," *Thymus* 5(2): 67–77 (1983), abstract only.
Dousa, "Cyclic–3',5'–nucleotide phosphodiesterase isozymes in cell biology and pathophysiology of the kidney," *Kidney Int.* 55(1): 29–62 (1999).

Epstein, et al., "Acute renal failure: a collection of paradoxes," *Hospital Practice Jan. 15, 1988*: 171–194.
Huber, et al., "Effect of theophylline on contrast material–induced nephropathy in patients with chronic renal insufficiency: controlled, randomized, double–blinded study," *Radiology* 223(3): 772–779 (2002).
Myers, et al., "Hemodynamically mediated acute renal failure," *N. Engl. J. Med.* 314(2): 97–105 (1986).
Pflueguer, et al., "Role of adenosine in contrast media–induced acute renal failure in diabetes mellitus," *Mayo Clin. Proc.* 75(12): 1275–8 (2000).
Prévot, et al., "Disparate effects of chronic and acute theophylline on cyclosporine A nephrotoxicity," *Pediatr. Nephrol.* 17(6): 418–24 (2002).
Shammas, et al., "Aminophylline does not protect against radiocontrast nephropathy in patients undergoing percutaneous angiographic procedures," *J. Invasive Cardiol.* 13(11): 738–40 (2001).
Welch, "Adenosine $A_1$ receptor antagonists in the kidney: effects in fluid–retaining disorders," *Curr. Opin. Pharmacol.* 2(2): 165–70 (2002).

* cited by examiner

*Primary Examiner*—Rebecca Cook
(74) *Attorney, Agent, or Firm*—Sonnenschein Nath & Rosenthal LLP

(57) ABSTRACT

Adenosine receptor antagonists, especially aminophyllline, are used to treat or prevent acute renal failure. In the preferred embodiment, aminophylline is administered by infusion so that it does not exceed a serum theophylline level of 15–20 micrograms/ml, most preferably the aminophylline is administered to achieve a serum theophylline concentration of 3–10 micrograms/ml, with an infusion rate of 0.1–0.6 mg/kg IBW/hour (IBW=ideal body weight). The adenosine receptor antagonist can also be used to help sustain a kidney for transplant purposes. Preferably, aminophylline is loaded while the kidney is still part of the donor. A dose of aminophylline of 5 mg/kg lean body weight is infused into the donor over a 30–60 min period, with cardiac monitoring. The infusion dose is decreased in the event of supraventricular or ventricular tachycardias. The kidney is removed and placed in the standard "cold" bath, but containing aminophylline at a dose of 5–10 micrograms/ml (5–10 mg/l). The kidney is then transported to the recipient. The recipient is similarly preloaded with 5 mg/kg lean body mass aminophylline intravenously over 30–60 min with cardiac monitoring, with a constant infusion of 0.1–0.3 mg/kg lean body mass/hr continuing during the next 24 hours after the kidney is transplanted into the recipient.

3 Claims, No Drawings

TREATMENT OR PREVENTION OF ACUTE RENAL FAILURE

This application claims benefit to U.S. Ser. No. 60/310,686 filed Aug. 8, 2001 and U.S. Ser. No. 60/352,075 filed Jan. 28, 2002.

BACKGROUND OF THE INVENTION

This is generally in the field of treatment or prevention of acute renal failure due to prerenal causes by administration of an antagonist of adenosine signaling, such as aminophylline, and of treatment of kidney transplants (renal allografts) to prolong survival of the graft during cold ischemia and immediately after transplantation.

Acute kidney failure occurs when illness, infection, or injury damages the kidneys resulting in a rapid decline in the kidneys' ability to clear the blood of toxic substances. Temporarily, the kidneys cannot adequately remove fluids and wastes from the body or maintain the proper level of certain kidney-regulated chemicals leading to an accumulation of metabolic waste products, such as urea, in the blood.

Acute kidney failure can result from any condition that decreases the blood supply to the kidneys (prerenal acute renal failure), obstructs the flow of urine after it has left the kidneys (postrenal acute renal failure), or injures the kidneys themselves (intra-renal acute renal failure). Toxic substances that may damage the kidneys include drugs, poisons, crystals precipitated in the urine, and antibodies that react against the kidneys. Symptoms depend on the severity of kidney failure, its rate of progression, and its underlying cause but can include anemia, bad breath, bone and joint problems, edema, frequent urination, hematuria, headaches, hypertension, fatigue, itching, lower back pain and nausea, and ultimately, death.

The condition that leads to the kidney damage often produces serious symptoms unrelated to the kidneys. For example, high fever, shock, heart failure, and liver failure may occur before kidney failure and may be more serious than any of the symptoms of kidney failure. Some of the conditions that cause acute kidney failure also affect other parts of the body. For example, Wegener's granulomatosis, which damages blood vessels in the kidneys, may also damage blood vessels in the lungs, causing a person to cough up blood. Skin rashes are typical of some causes of acute kidney failure, including polyarteritis, systemic lupus erythematosus, and some toxic drugs. Hydronephrosis can cause acute kidney failure resulting from obstruction of urine flow.

Acute kidney failure can be caused by many different illnesses, injuries, and infections. These conditions fall into three main categories: prerenal, postrenal, and intrarenal conditions. Prerenal conditions do not damage the kidney, but can cause diminished kidney function. They are by far the most common cause of acute renal failure, and include dehydration, hemorrhage, septicemia, heart failure, liver failure, and burns. Approximately 95% of acute renal failure in the hospital is prerenal, due to decreased renal blood flow due to intravascular volume depletion or cardiac pump failure. A common cause of prerenal acute renal failure outside the hospital is rhabdomyolysis: muscle breakdown caused by a crush injury, as in an earthquake, or prolonged marching by soldiers. In out-of-hospital situations such as these, access to a kidney dialysis machine is often unavailable.

Postrenal conditions cause kidney failure by obstructing the urinary tract and include inflammation of the prostate gland in men (prostatitis), enlargement of the prostate gland (benign prostatic hypertrophy), bladder or pelvic tumors, and kidney stones (calculi). Intrarenal conditions involve kidney disease or direct injury to the kidneys. These conditions include lack of blood supply to the kidneys (ischemia), use of radiocontrast agents in patients with kidney problems, drug abuse or overdose, long-term use of nephrotoxic medications, acute inflammation of the glomeruli, or filters, of the kidney (glomerulonephritis), kidney infections (pyelitis or pyelonephritis).

Acute kidney failure and its immediate complications can often be treated successfully. The survival rate ranges from less than 50 percent for people who have failure of several organs to about 90 percent for those who have decreased blood flow to the kidneys because body fluids have been lost through bleeding, vomiting, or diarrhea. Treatment for acute kidney failure varies. Treatment is directed to the underlying, primary medical condition that has triggered kidney failure. Prerenal conditions may be treated with replacement fluids given through a vein, diuretics, blood transfusion, or medications. Postrenal conditions and intrarenal conditions may require surgery and/or medication.

Often, simple but meticulous treatment is all that is required for the kidneys to heal themselves. In addition to glucose or highly concentrated carbohydrate feedings, certain amino acids are given orally or intravenously to maintain adequate protein levels. The intake of all substances that are eliminated through the kidneys, including many drugs such as digoxin and some antibiotics, must be strictly limited. Because antacids that contain aluminum bind phosphorus in the intestines, they may be given to prevent the blood phosphorus level from rising too high. Sodium polystyrene sulfonate is sometimes given orally or rectally to treat a high blood level of potassium.

Kidney failure may be so severe that dialysis is needed to prevent serious harm to other organs and to control symptoms. In these cases, dialysis is started as soon as possible after diagnosis. Dialysis may be needed only until the kidneys recover their function, usually in several days to several weeks. However, if the kidneys are too badly damaged to recover, dialysis may be needed indefinitely, unless kidney transplantation is performed. Dialysis for acute renal failure, however, is extremely expensive and carries a high mortality rate (50%) that has remained unchanged despite advances in dialysis. The natural course of oliguric acute renal failure is to progress to acute tubular necrosis, a state of near-total kidney failure that requires renal replacement therapy.

Acute renal failure (ARF) continues to defy efforts at therapy, and carries a 50% mortality. It has long been known to involve renal vasoconstriction, having been called "vasomotor nephropathy" since the 1960's (Myers, et al., N.E.J. Med. 314:97–105, 1986). Over several decades. Dr. Franklin Epstein has documented the role of ischemia, especially of the medullary thick ascending limb, in the pathogenesis of ARF (Epstein, et al., Hospital Practice Jan. 15, 1988: 171–194, passim). ARF is a clinical syndrome marked by an abrupt and sustained decrease in renal function which occurs in response to an ischemic or nephrotoxic insult, and which is not immediately reversible upon correction of the precipitation event. ARF can lead to life-threatening complications such as uremia, sepsis, gastrointestinal hemorrhage, and central nervous system dysfunction. It is associated with a high mortality rate and may be a major factor in determining the outcome of multi-organ failure. For example, in one study of similarly traumatized patients, those who developed acute renal failure had a five-fold higher mortality rate than those who did not. A high percentage of patients with ARF will require invasive life-sustaining therapy with dialysis—with its associated risk of bleeding complications, arrhythmias, hypotension, additional cost, and negative impact on quality of life. ARF is also associated with prolongation of hospitalization, and significantly complicates the care of severely ill patents by limiting the fluids and medications that may be administered to them. In addition, a significant number of patients surviving ATN (acute tubular necrosis) are left with residual renal insufficiency.

At present there is no therapy available for the treatment of ATN other than supportive care. Physicians frequently use diuretics such as furosemide or mannitol, and/or "renal dose" dopamine empirically with the hope of increasing urine output, but none of these agents have been shown to improve renal function significantly nor decrease the morbidity and mortality, as well as the expense associated with this disease. Recovery from ATN may last from weeks to months, in proportion to a patient's age. In the meantime, acute dialysis is required on at least a trice-weekly basis. It would therefore represent a considerable savings, both in health care dollars as well as lives, if ATN could be quickly aborted pharmacologically.

A method of treatment that can prevent damage during acute renal failure is needed.

It is therefore an object of the present invention to provide a treatment to prevent or treat acute renal failure.

It is another object of the present invention to provide a treatment to enhance viability of kidneys for transplant purposes.

SUMMARY OF THE INVENTION

Adenosine receptor antagonists, especially aminophyllline, are used to treat or prevent acute renal failure. Adenosine antagonists are suited for prerenal acute renal failure only. The treatment obviates the need for dialysis in over 50% of patients with acute renal failure which has progressed to the point of oliguria (less than 300 ml urine output per day, or less than 100 ml urine output per 8 hours). The treatment is intended to be started during the late stage of acute renal failure, after restoration of intravascular volume has failed to increase urine output and lower serum creatinine levels, but before acute tubular necrosis has supervened. In the preferred embodiment, aminophylline is administered by infusion so that it does not exceed a serum theophylline level of 15–20 micrograms/ml, most preferably the aminophylline is administered to achieve a serum theophylline concentration of 3–10 micrograms/ml, with an infusion rate of 0.1–0.6 mg/kg IBW/hour (IBW=ideal body weight).

The adenosine receptor antagonist can also be used to help sustain a kidney for transplant purposes. Preferably, aminophylline is loaded while the kidney is still part of the donor. A dose of aminophylline of 5 mg/kg lean body weight is infused into the donor over a 30–60 min period, with cardiac monitoring. The infusion dose is decreased in the event of supraventricular or ventricular tachycardias. The kidney is removed and placed in the standard "cold" bath, but containing aminophylline at a dose of 5–10 micrograms/ml (5–10 mg/l). The kidney is then transported to the recipient. The recipient is similarly pre-loaded with 5 mg/kg lean body mass aminophylline intravenously over 30–60 min with cardiac monitoring, with a constant infusion of 0.1–0.3 mg/kg lean body mass/hr continuing during the next 24 hours after the kidney is transplanted into the recipient.

DETAILED DESCRIPTION OF THE INVENTION

I. Compositions for Treatment or Prevention of Acute Renal Failure

Adenosine A(1) receptor antagonists are used to treat or prevent acute renal failure. In the preferred embodiment, the patient is treated with aminophylline (amoline, somophyllin, aminophyllin). Aminophylline is in the class of Xanthine bronchodilators that includes theophylline and caffeine. This drug is approved for the treatment of asthma, apnea and braycardia spells although new research indicates a role in renal vasodilation. It affects the breathing center of the brain and achieves bronchodilation via different mechanisms than sympathomimetics thus being effective when sympathomimetics are not. It may also increase the muscle activity of the diaphragm. Both aminophylline and theophylline have the same active ingredient and are used interchangeably. Aminophylline is given by vein and theophylline is given by mouth. In addition to bronchodilation, aminophylline is a respiratory stimulant; it has mild diuretic properties, and positive chronotropic and positive inotropic effects (in large doses). In emergency care, aminophylline is usually administered by slow intravenous infusion.

Aminophylline has been reduced to a second-line drug in the emergency setting due to more efficacious agents and controversy over its usefulness in treating asthma. Outside of commonly known bronchdilators (e.g. Ventalin) which activate alpha-adrenergic receptors, xanthine or theophylline-type drugs act differently by preventing the degradation of cAMP, thereby keeping the airways open. Contraindications of Aminophylline include allergy to xanthine compounds (for example, caffeine), hypersensitivity to the drug and cardiac dysrhythmias. Adverse reactions have been reported that include tachycardia, palpitations, PVCs, angina pectoris, dizziness, anxiety, headache, seizure, nausea and vomiting, abdominal cramps.

Adenosine A(1) receptor antagonists have been used effectively as potassium-sparing and renal-function-protective diuretics in new studies. Aminophylline is a widely available adenosine antagonist that blocks both adenosine A1 and adenosine A2 receptors. Specific adenosine A1 receptors can signal, through Gi/o proteins, to inhibit adenylyl cyclase activity and also to stimulate phosphoinositide hydrolysis and the subsequent release of intracellular Ca2+ stores resulting in renal vasoconstriction. A(1) receptor activation would therefore exacerbate cases of acute renal failure (ARF). Glycerol-induced ARF results in increased expression of renal adenosine A(1) receptors in the cortex and reduced expression in the inner medulla of the kidney. Increased density of A(1) receptors in glomeruli may account, at least in part, for the increased renal vasoconstrictor response to adenosine and depressed glomerular filtration rate noted previously in this type of acute renal failure. An increase in adenosine A1 receptor density in renal resistance vessels may explain, at least in part, the enhanced renal vasoconstrictor response to adenosine in glycerol-induced ARF that was noted in a previous study.

The application of adenosine receptor antagonists has been implicated in protection from acute renal failure. Aminophylline and Theophyllin E, two non-selective adenosine-competitive inhibitors, were evaluated as potential agents to protect against radiocontrast nephropathy (RCN) (Shammas et al J Invasive Cardiol November 2001; 13(11):738–40; Welch et al Curr Opin Pharmacol April 2002; 2(2):165–70; Huber et al. Radiology June 2002; 223(3):772–9). Aminophylline does not appear to add a protective role in preventing RCN while Theophyllin E was effective in preventing RCN impaired renal excretory, endocrine and tubular function. These results suggest that adenosine may play a role in the pathogenesis of RCN and that application of adenosine receptor antagonists has been implicated in protection from acute renal failure associated with radiocontrast media treatment. In cyclosporin-A-induced renal failure, where renal vasoconstriction is also observed, theophylline restored renal function significantly (Prevot et al. Pediatr Nephrol June 2002; 17(6):418–24).

Increased release of renal adenosine and stimulation of renal adenosine receptors have been proposed to be major mechanisms in the development of contrast media-induced acute renal failure (CM-ARF) (Pflueguer et al. Mayo Clin Proc December 2000; 75(12):1275–8). Patients with diabetes mellitus or preexisting renal disease who have reduced renal function have a markedly increased risk to develop CM-ARF. Furthermore, recent evidence suggests that administration of adenosine receptor antagonists reduces the risk of development of CM-ARF in both diabetic and nondiabetic patients.

Investigations of recent years revealed that isozymes of cyclic-3',5'-nucleotide phosphodiesterase (PDE) are a critically important component of the cyclic-3',5'-adenosine monophosphate (cAMP) protein kinase A (PKA) signaling pathway (Dousa Kidney Int January 1999; 55(1):29–62). The super family of cyclic-3',5'-phosphodiesterase (PDE) isozymes consists of at least nine gene families (types): PDE1 to PDE9. PDE isozymes also play an important role in the pathogenesis of acute renal failure of different origins. Administration of PDE isozyme-selective inhibitors suppresses some components of immune responses to allograft transplant and improves preservation and survival of transplanted organs In ARF due both to sepsis and to the hepatorenal syndrome (which carry close to 100% mortality), the renal circulation is paradoxically vasoconstricted, despite profound vasodilation of the systemic circulation (SVR<800, systolic blood pressure often below 100 mm Hg). Attempts to perfuse the kidney by increasing the intravascular volume (the "effective intra-arterial blood volume," a concept popularized by Dr. Robert Schrier) have no effect on the rising serum creatinine and BUN, and, in the case of sepsis, results in intolerable pulmonary edema from "capillary leak" syndrome. The method described herein "opens up" the renal circulation pharmacologically, after the more physiologic method of fluid replacement has been tried and failed.

Although numerous renal vasoconstrictor agents are known, and many more probably remain to be discovered (such as adrenomedullin, and various lipid products), only one agent is known to be capable of the paradox of simultaneous systemic vasodilation and profound renal vasoconstriction. It is adenosine, operating through A1 receptors in the kidney cortex to produce renal cortical vasoconstriction, and A2 receptors in the renal medulla and the rest of the systemic circulation, including the coronary arteries, to cause vasodilation. Adenosine is produced from ATP (adenosine triphosphate) and ADP (adenosine diphosphate) under conditions of ischemia. Adenosine is therefore useful for mediating the ARF of hepatorenal syndrome and sepsis, both of which are characterized by low FENa (fractional excretion of sodium) arid a "prerenal" picture. In hepatorenal syndrome, the dying liver may be supplying massive quantities of adenosine to the systemic circulation. In sepsis, ischemic muscle and viscera (including the liver) may likewise be providing adenosine to the systemic circulation. More generally, adenosine may mediate tubulo-glomerular (T-G) feedback. It is wll known that increased chloride delivery to the distal tubule, near the region of the macula densa, induces potent vasoconstriction of the afferent renal arteriole. Renin, present in the juxtaglomerular apparatus (JGA), cannot mediate this phenomenon, since its release is triggered by a decrease in NaCl delivery to the JGA. Adenosine, which may result from exhaustion of ATP supplies in the thick ascending limb as a result of the increased pumping demanded by increase ion delivery to this segment, is an excellent candidate to mediate T-G feedback, it can directly link chemical work in the critical nephron segment (the medullary thick ascending limb) to blood flow in the glomerulus, which is the start of the "conveyor belt" for the nephron; it is a potent renal cortical vasoconstrictor, and it is short-lived, allowing for rapid and sensitive regulation.

If adenosine generally mediates T-G feedback, then blockade of renal A1 receptors will ameliorate vasomotor nephropathy in acute renal failure. Although specific A1 antagonists are not yet clinically available, aminophylline is a non-specific antagonist of both A1 and A2 receptors with great familiarity for clinicians. In addition, by antagonizing cyclic aminophylline phohpodiesterase, aminophylline prevents transformation of cyclic aminophylline into adenosine, which is a major route of metabolism of cyclic aminophylline in some tissues. In rat models of glycerol-induced ARF as well as human trials to prevent radio-contrast renal injury, IV aminophylline has been dramatic in preventing ARF if administered before the toxic insult.

Radiocontrast renal injury is now relatively rare and appears entirely preventable by adequate intravenous hydration before and after the radiocontrast insult. The present treatment is for acute renal failure due to prerenal causes but which is unlike radiocontrast renal injury 9in that (1) it has occurred without warning, and (2) it has progressed despite adequate restoration of intravascular volume.

II. Method of Treatment

Treatment of Acute Renal Failure

In the preferred embodiment, subjects with ATN (as defined by the inclusion and exclusion criteria) 48 hour intravenous of either aminophylline. Renal function, dialysis requirements and mortality are monitored for up to 21 days. A subject's history, physical examination, assessment of fluid status (including central hemodynamic monitoring, if available), and laboratory tests (including urinary parameters, if appropriate) are used to determine if acute renal dysfunction is due to ATN or to other causes (such as postrenal, acute renovascular obstructive etiologies, or intrinsic renal/systemic diseases other than ATN such as glomerulonephritis or vasculitis). The following are symptoms of acute renal failure: evidence of an acute progressive rise in serum creatinine (at least 50% increase within 24 hours preceding enrollment) without stabilization or recovery, despite optimization of hemodynamic fluid status and correction of any known pharmacologic, pre-renal, or post-renal etiologic factors. PCWP m12 cm H20; Cardiac Index>1.5; and Systolic BP>100 (with or without pressor support). The following are reasons to exclude patients: Non-oliguric ATN (urine output>500 ml/day, or >20 ml/hour); Oliguria due to uncorrected pre-renal azotemia (indicated by oliguria, FENa of less than 1% and absence of granular casts in the urine); history of chronic renal insufficiency with SCr>4.0 mg/dl (352 μmol/L); history of renal transplantation; patients whose non-renal medical condition is so severe that they are being allowed to die; patients who have a systolic blood pressure of less than 100 mmHg even with pressor support; and presence of any condition or therapy which, in the opinion of the Investigator, may cause administration of aminophylline to pose a significant risk to the patient, such as status epilepticus, serious ventricular arrhythmia, ongoing angina, etc. Other potential reasons for exclusion include ARF due to causes other than ATN, such as post-renal obstruction, systemic disease, or renovascular obstruction; ARF due to intrinsic renal disease or systemic disease (acute interstitial nephritis, vasculitis, glomerulonephritis, lupus nephritis, cyclosporine toxicity, etc.); ARF due to acute bilateral renal vascular obstruction (dissecting aortic aneurysm, acute thrombosis/embolism, etc.); ARF due to ongoing post-renal obstruction. (Note: Renal ultrasound must be performed if obstruction is suspected; it is expected that an indwelling bladder catheter will be used to quantitate hourly urine output for at least a few hours before and following the initiation of this study)

In the preferred embodiment, the rate of aminophylline infusion will be adjusted so as never to exceed a serum theophylline level of 15–20 micrograms/ml, as is currently the practice for bronchospasm. In fact, a target serum theophylline concentration of 3–10 micrograms/ml will be striven for, using an infusion rate of 0.1–0.6 mg/kg IBW/ hour (IBW=ideal body weight). At no point will the infusion rate be increased above 0.6 mg/kg IBW/hour. 0.3 mg/kg IBW/hour is the "low dose" regimen of intravenous aminophylline recommended to minimize toxicity for patients with bronchospasm and hepatic insufficiency or severe congestive heart failure (CHF). The dose may be modified by the physician as needed for toxicity or other adverse events. Patients should receive the usual standard supportive care for acute renal failure including optimization of fluid and nutritional status, administration of medications and therapies as needed for the treatment of other ongoing medical problems, discontinuation or minimization of the use of nephrotoxic agents, and adjustment of medication doses as appropriate for the level of renal dysfunction. Diuretics (such as furosemide and mannitol) or "renal dose" dopamine (1–2 ug/kg/min) may be utilized but are not preferred. The need for a patient to undergo dialytic therapy will be determined by each subject's attending nephrologist on a case-by-case basis according to existing clinical standards for uremia, volume overload, electrolyte imbalance and/or acid base disturbances not responsive to medical management.

The only known risks to the patient will be those associated with aminophylline toxicity, such as nausea and vomiting (usually at serum theophylline levels around 20 micrograms/ml), tachyarrhythmias (usually supraventricular but including ventricular tachycardia—at serum theophylline levels above 30–40 micrograms/ml). Aminophylline-induced tachyarrhythmias can usually be reversed with intravenous adenosine.

GENERAL DEFINITIONS

Adverse Experience: A noxious, pathologic or unintended change in anatomic, physiologic, or metabolic function as indicated by physical signs, symptoms, and/or laboratory changes associated with the use of a drug or placebo in humans, and whether or not considered drug related. This includes an exacerbation of a pre-existing condition or event and the unusual failure of expected pharmacologic action.

Serious Adverse Experience: Any experience which suggests a significant hazard, contraindication, side effect, or precaution. This includes any experience that is fatal or life threatening, is permanently disabling, requires inpatient hospitalization (or prolongation of hospitalization), or is a congenital anomaly, cancer, or overdose.

III. Treatment to Improve the Function of Renal Allografts

Aminophylline and other adenosine antagonists can also be used to improve the function of renal allografts. As many as 50% of kidney transplants have initial graft dysfunction. In up to a third of kidney grafts, interim dialysis is required. It is recognized that cold ischemic time is an important variable in the incidence of initial graft dysfunction. In fact, grafts are discarded after 24 hr, when the incidence of initial and prolonged graft failure is unacceptably high.

In oliguric acute renal failure, aminophylline is able to reverse the ischemia and vasoconstriction due to tubuloglomerular feedback, through antagonism of adenosine A1 and A2 receptors (especially vasoconstrictive A1 receptors). The same mechanism can be employed to counteract the vasoconstriction and ischemia due to non-perfusion of the kidney transplant.

Preferably, aminophylline is loaded while the kidney is still part of the donor. A dose of aminophylline of 5 mg/kg lean body weight is infused into the donor over a 30–60 min period, with cardiac monitoring. The infusion dose is decreased in the event of supraventricular or ventricular tachycardias.

The kidney is removed and placed in the standard "cold" bath, but containing aminophylline at a dose of 5–10 micrograms/ml (5–10 mg/l). The kidney is then transported to the recipient. This technique should make possible the use of kidneys after 48–72 hours of "cold ischemia" time, i.e. more than the 24 hrs currently feasible. This will have the net effect of increasing the number of available kidneys for transplantation; fewer will need to be discarded.

The recipient is similarly pre-loaded with 5 mg/kg lean body mass aminophylline intravenously over 30–60 min with cardiac monitoring, with a constant infusion of 0.1–0.3 mg/kg lean body mass/hr continuing during the next 24 hours after the kidney is transplanted into the recipient.

This method will decrease the incidence of initial graft failure, and with it the enormous morbidity and expense associated with interim dialysis after renal transplantation.

Modifications and variations of the method and compositions described herein will be obvious to those skilled in the art and are intended to come within the scope of the appended claims.

I claim:

1. A method to treat prerenal acute renal failure comprising administering an effective amount of an adenosine receptor antagonist to a human patient with prerenal acute renal failure, wherein the adenoaline receptor atagonist is aminophylline, and wherein the aminophylline is administered by infusion to achieve a target serum theophylline concentration of 3–10 micrograms/ml.

2. The method of claim 1, wherein the adenosine receptor antagonist is infused with an infusion rate of 0.1–0.6 mg/kg ideal body weight/hour.

3. The method of claim 1 wherein the acute renal failure has progressed to the point of oliguria, after restoration of intravascular volume has failed to increase urine output and lower serum creatinine levels but before acute tubular necrosis has supervened.

* * * * *